United States Patent [19]
Richards

[11] Patent Number: 5,634,918
[45] Date of Patent: Jun. 3, 1997

[54] OPHTHALMIC SURGICAL INSTRUMENT

[75] Inventor: William D. Richards, Marietta, Ga.

[73] Assignee: Grieshaber & Co. AG Schaffhausen, Schaffhausen, Switzerland

[21] Appl. No.: 328,988

[22] Filed: Oct. 26, 1994

[51] Int. Cl.⁶ .................................................. A61B 17/28
[52] U.S. Cl. ........................ 606/1; 606/205; 606/166
[58] Field of Search ........................... 606/1, 107, 166, 606/167, 171, 174, 205, 206; 81/177.1, 489; 401/99, 183, 209

[56] References Cited

U.S. PATENT DOCUMENTS

| | | | |
|---|---|---|---|
| 3,133,526 | 5/1964 | Sears | 401/99 X |
| 3,576,374 | 4/1971 | Lile | 401/99 X |
| 4,655,219 | 4/1987 | Petruzzi | 606/206 X |
| 5,082,000 | 1/1992 | Picha et al. | 128/751 |
| 5,133,727 | 7/1992 | Bales et al. | 606/170 |
| 5,211,652 | 5/1993 | Derbyshire | 606/182 |
| 5,222,973 | 6/1993 | Sharpe et al. | 606/206 |
| 5,224,954 | 7/1993 | Watts et al. | 606/205 |

OTHER PUBLICATIONS

ASSI brochure, "Vitrectomy Instruments from ASSI", author unknown, 1 page, 1994.
DORC brochure, "DORC Microforceps and Microscissors", data and author unknown, 1 page.
Nataloni, "Technology is the method of vit/ret surgeons", Ocular Surgery News, 1 page.
Synergetics, Inc. brochure, "Synerlite", date and author unknown, 1 page.

Primary Examiner—Guy V. Tucker

[57] ABSTRACT

An ophthalmic surgical instrument operates a tool such as a scissors, a forceps or a knife. The instrument has an actuator with a generally cylindrical actuation surface; the actuator is operated by pressure applied to any point on the surface. The resulting instrument can be easily rotated about its axis whether in the operated or unoperated states.

12 Claims, 6 Drawing Sheets

5,634,918

OPHTHALMIC SURGICAL INSTRUMENT

BACKGROUND OF THE INVENTION

The invention relates to handheld tools, and more specifically relates to handheld tools of the mechanically operable type. In its most immediate sense, the invention relates to ophthalmic surgical instruments of the Sutherland type.

Eye surgery requires the use of forceps, scissors etc. within the eye. Typically, a surgeon will make an incision in the eye and will then introduce a surgical instrument, e.g. a scissors, in the incision. The surgeon will then operate the scissors by actuating the tool.

A Sutherland-type instrument has a pen-type handle and uses a lever as an actuator. A variety of mechanically operable spring-loaded tools, e.g. scissors, forceps, knives etc. can be threaded onto the front tip of the handle immediately adjacent the lever. A surgeon operates the tool (i.e. opens and closes the forceps or scissors) by depressing the lever using his thumb or index finger. Such depression operates the tool against the pressure of its internal spring. After operating the tool, the surgeon releases the lever arm, causing the tool to return to its original state.

This type of surgical instrument has disadvantages. One such disadvantage is that keeping the instrument in the operated state (e.g. keeping a forceps in the closed position) while rotating the tool 180° often forces the surgeon to assume an awkward posture and/or to use two hands when only one hand is conveniently free. Another disadvantage is that the instrument cannot conveniently be operated in all rotational positions, i.e. the tool cannot easily be operated unless the lever arm is e.g. adjacent the surgeon's index finger.

It would therefore be advantageous to provide a Sutherland-type instrument which could be easily and conveniently rotated about its axis even when in the operated state.

It would additionally be advantageous to provide a Sutherland-type instrument which could easily be operated in all rotational positions.

It would further be advantageous to provide a Sutherland-type instrument which could be used to operate tools designed to fit with existing Sutherland-type instruments, but which additionally would be suitable for operation in all rotational positions and which could be easily and conveniently rotated about its axis even when in the operated state.

In accordance with the invention as implemented in a pen-type tool, the actuator of a pen-type instrument is located at the end of an elongated handle. The actuator has an actuation surface which extends completely around the axis of the handle. The actuator is operated by applying pressure anywhere on this actuation surface. Because the actuation surface can be actuated at any point, there is no need to position an actuator lever adjacent the surgeon's index finger or thumb, and there is no difficulty in rotating the instrument while the actuator is operated.

In accordance with an alternate embodiment of the invention, the actuator has a mechanical advantage which is greater than unity, i.e. a small movement of the actuator causes a larger movement of the tool. This amplifies a surgeon's relatively small squeezing or pressing motion to a relatively large motion of the threaded-on tool.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

Figure 1:
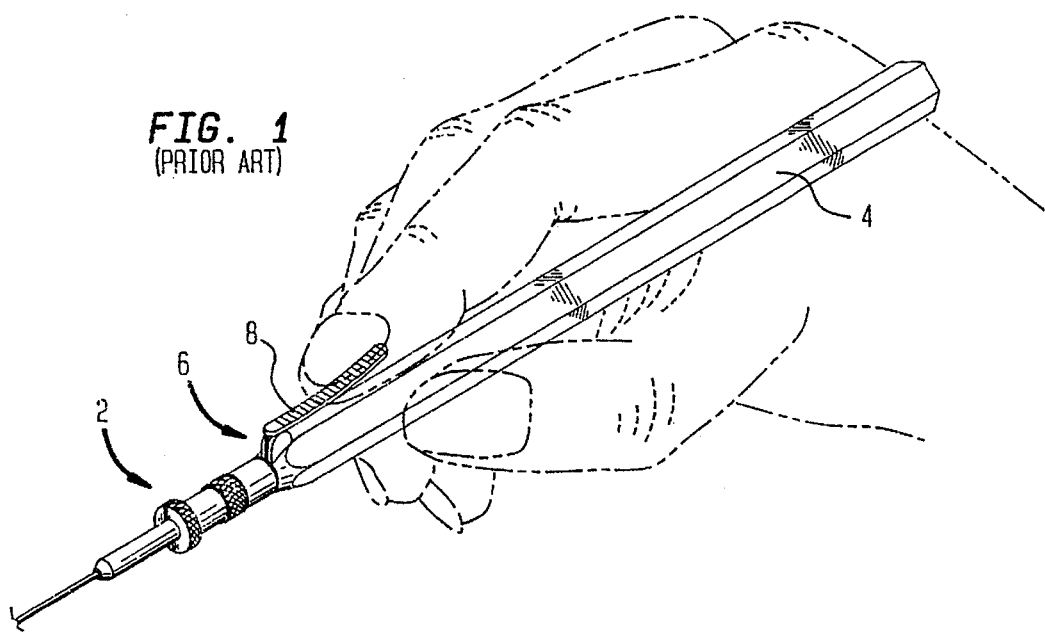
FIG. 1 shows a known Sutherland-type instrument.
Figure 2:
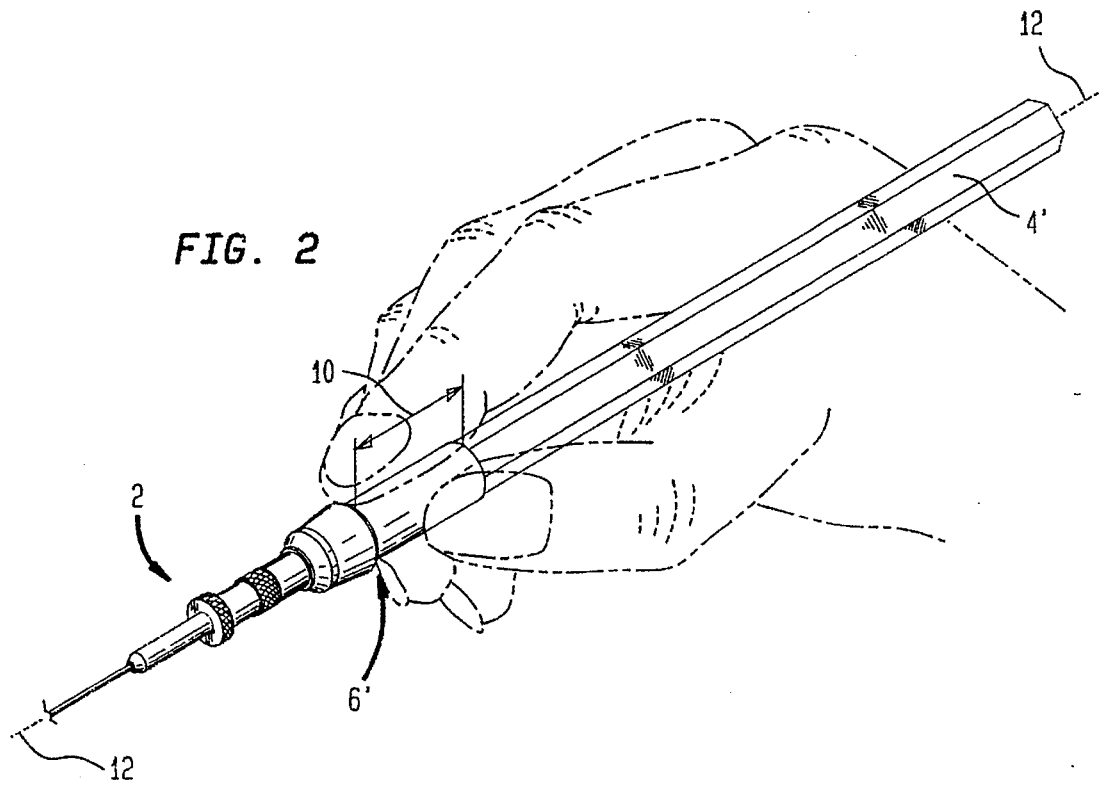
FIG. 2 shows an exterior view of an embodiment in accordance with the invention.

In all figures, the same element is always indicated using the same reference numeral. The same or similar parts in the several embodiments are cross-referenced using primed reference numerals. The Figures are not to scale and some dimensions are exaggerated for clarity.

During most eye surgery, the surgeon makes an incision in the eye and introduces a mechanically operable tool in the incision. Typical tools are forceps, scissors, knives etc.

In a Sutherland-type instrument system such as is sold in the United States through Grieshaber & Co., Inc. (see FIG. 1), such tools 2 are detachably securable to the threaded end of a handle 4. This permits selected ones of a variety of available tools to be threaded onto the handle 4, used, and removed for cleaning. To operate the tool 2, the handle 4 is provided with an actuator 6 which takes the form of a pivoted lever having an interior end (not shown, for operating the tool) and an exterior end 8 (for operation by the surgeon's thumb or index finger). When the tool 2 is threaded onto the end of the handle 4, an interior spring-loaded plunger (not shown) in the tool 2 is urged against the interior end of the actuator 6. When a surgeon depresses the exterior end 8 of the actuator 6 using his index finger or thumb, the actuator 6 pivots. As a result, the interior end presses against the plunger and operates the tool 2 against the pressure of its interior spring (not shown). Such operation can be repeated by repeatedly pressing the exterior end 8 and releasing it.

It is awkward and inconvenient for a surgeon to rotate the tool while maintaining it in its operated position. Either the surgeon must rotate his entire hand and arm while keeping e.g. his index finger depressed, or the surgeon must somehow rearrange his fingers so that at least one finger depresses the actuator 6 in all rotational positions of the instrument.

Additionally, when the instrument is lying on a work surface and the surgeon wishes to use it, the surgeon must not only rotate the instrument to a position in which the lever is in the proper position but must also rotate the tool 2 itself so that the tool 2 is properly oriented. By way of example, let it be assumed that the tool 2 is a scissors which is oriented at 12:00 in the instrument tray (not shown). Let it further be assumed that the surgeon wishes to use the scissors at the 3:00 orientation. To do this, the surgeon must pick up the instrument, revolve it in his hand until the instrument is in a comfortable position and then spin the tool 2 to the 3:00 orientation while holding the handle 4 fixed.

In accordance with the invention as implemented in a pen-type ophthalmic instrument, a pen-type instrument has an elongated handle 4' with an actuator 6' at one end. The actuator 6' has an actuation surface 10 which extends completely around the axis 12 of the handle 4'; advantageously, the actuation surface 10 is generally cylindrical and coaxial with the axis 12 of the handle 4'. Advantageously but not necessarily, the actuation surface 10 is an elastomeric boot 12 which seals the actuator 6' and prevents foreign matter from entering and obstructing the mechanism. The actuator 6' is operated by applying pressure anywhere on the actuation surface 10. Thus, a surgeon who picks up the instrument with the actuator 6' between his thumb and index finger can easily and conveniently rotate the tool whether it is in the operated or unoperated state. Such rotation is easily accomplished by rolling the actuator 6' between the thumb and index finger; operation and release of the tool 2 is easily accomplished by respectively squeezing and releasing the actuator 6'. It is alternatively possible to operate the actuator 6' by holding the handle 4' and pressing the actuation surface 10 of the actuator 6' with the thumb or index finger.

Two embodiments of the invention will now be described. The preferred embodiment of the actuator 6' will be described first with reference to FIGS. 3, 3A and 4 and an alternate embodiment of the actuator 6' will be described next with reference to FIGS. 5 and 6.

Figure 3:
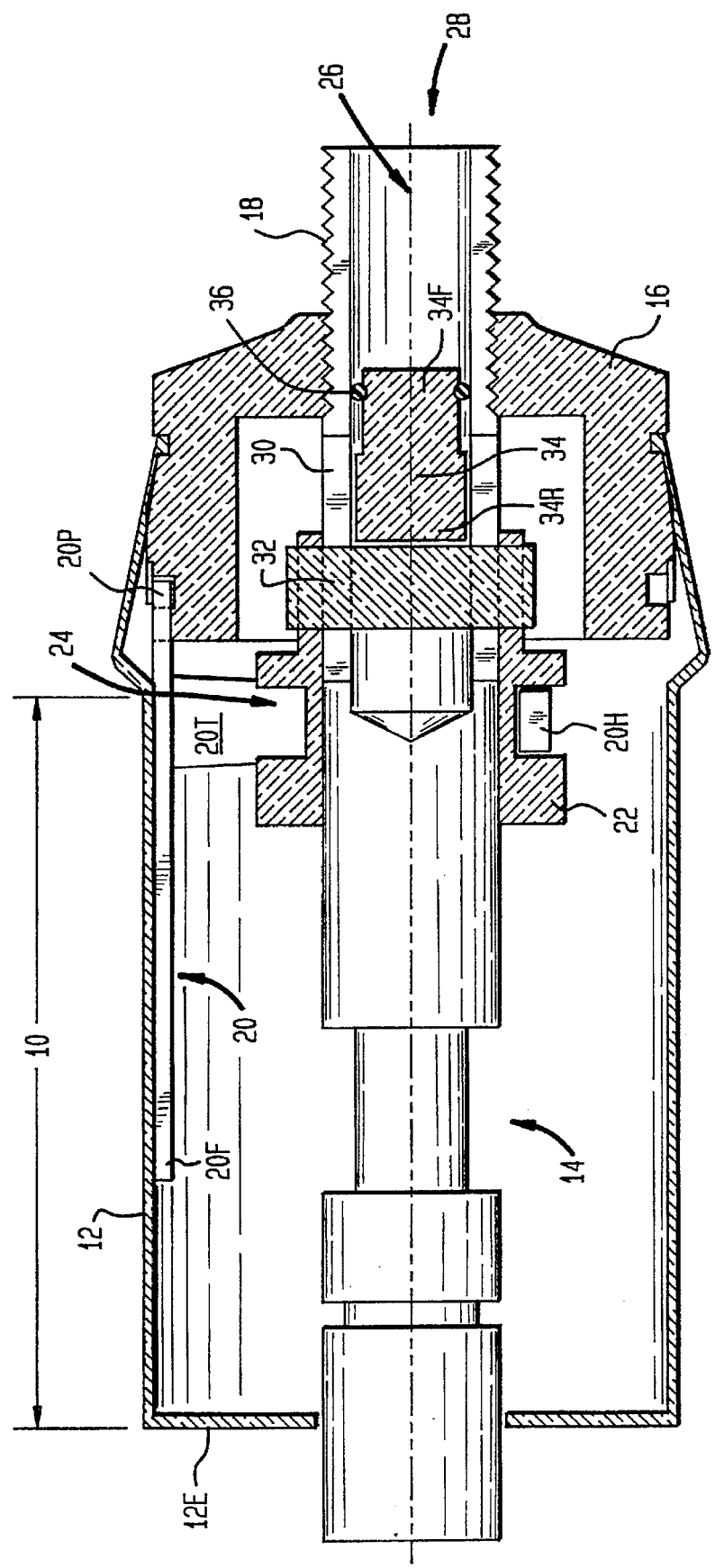
FIG. 3 shows a cross-sectional view of a preferred embodiment in the unactuated state.
Figure 3A:
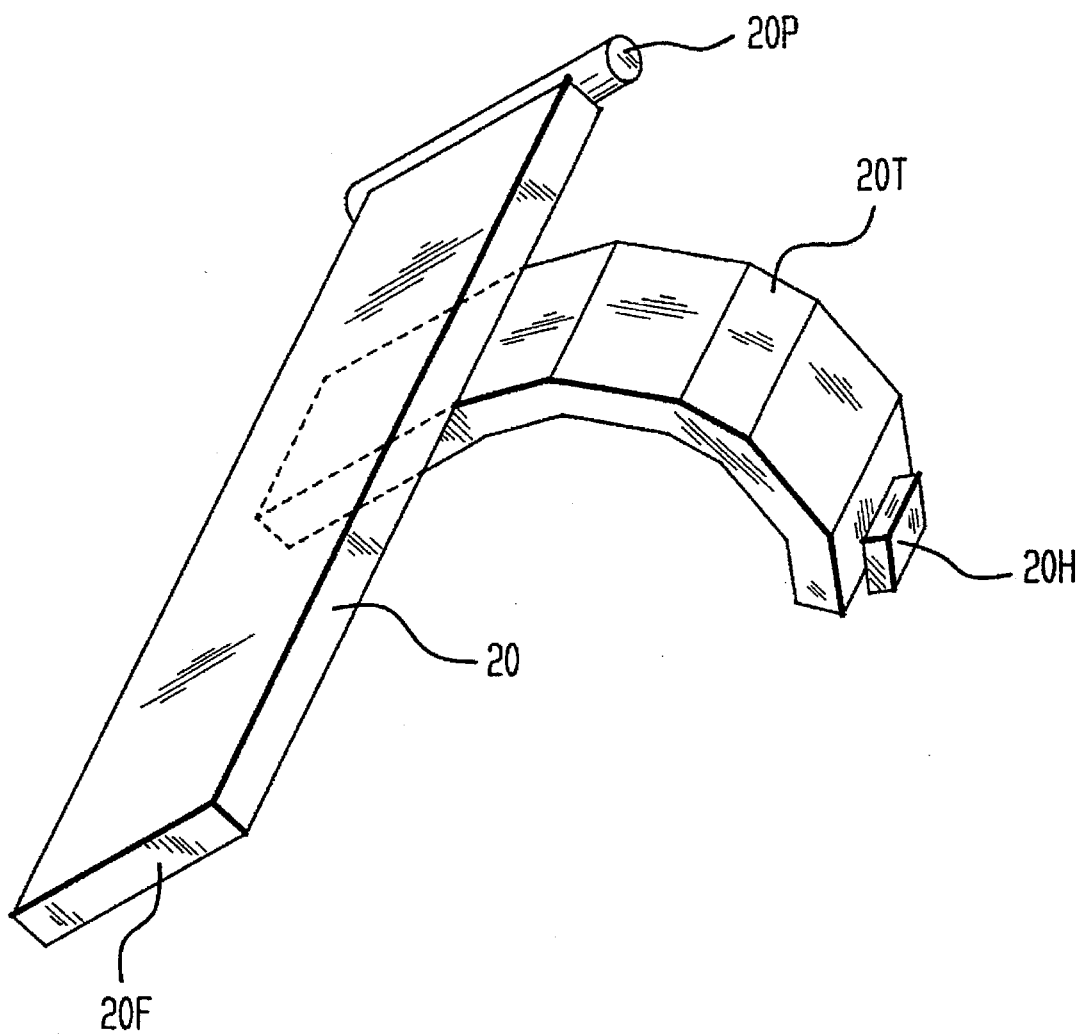
FIG. 3A shows an end view of a trigger in accordance with an embodiment of the invention.
Figure 4:
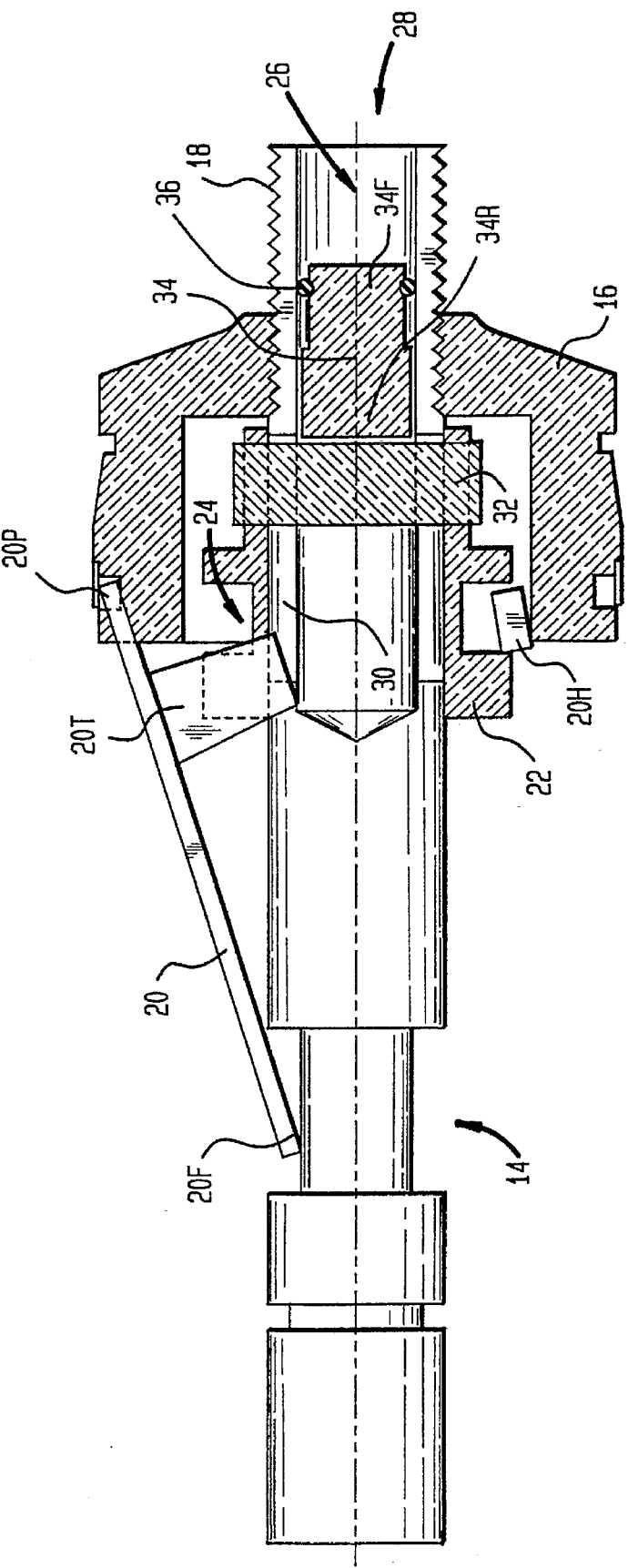
FIG. 4 shows a cross-sectional view of the FIG. 3 embodiment in the actuated state, without the elastomeric boot.

A central axially elongated rod 14 supports a nose piece 16, which is fixed to the forward end 18 of the rod 14. Six triggers 20 (for clarity, only one is shown in FIGS. 3 and 4) are pivotally secured to the nose piece 16. Each trigger 20 has a pivot end 20P, a free end 20F and a tie arm 20T; each tie arm 20T is curved to circulate around the rod 14, and each tie arm 20T has a hook 20H at its distal end (see FIG. 3A). The boot 12 fits over the nose piece 16 and triggers 20 and is sufficiently elastic to permit the triggers 20 to move radially inwardly and outwardly.

A trigger retainer 22 is slidably mounted upon the rod 14. The trigger retainer 22 is a hollow sleeve which has an annular grooved region 24 on its radially outer surface. The grooved region 24 receives the hooks 20H at the ends of the six tie arms 20T from the six triggers 20; the hook 20H from each tie arm 20T is disposed within the grooved region 24.

Each trigger 20 is pivotally mounted at its pivot end 20P to the nose piece 16. When the free end 20F of any trigger 20 is pressed radially inwardly towards the rod 14, the hook 20H at the end of the tie arm 20T presses against the grooved region 24 and urges the trigger retainer 22 to the right as viewed in FIGS. 3 and 4. This causes all the triggers 20 to simultaneously move radially inwardly. Likewise, when spring pressure urges the trigger retainer 22 to the left as viewed in FIGS. 3 and 4, the free ends 20F of all the triggers 20 are simultaneously moved radially outwardly, away from the rod 14. It may therefore be understood that radially inward and outward motion of any one of the triggers 20 is converted respectively to rightward and leftward translation of the trigger retainer 22 and is accompanied by like simultaneous movement of all the other triggers 20.

The rod 14 has an axially extending bore 26 which is open at the forward end 28 and which extends rearwardly from the forward end 28. The rod 14 also has an axially elongated slot 30 which passes entirely through the rod 14 and which intersects the bore 26 near its bottom. A pin 32 is secured to the trigger retainer 22 (as by force-fitting into two diametrically opposed holes) and passes through the slot 30 so as to extend radially with respect to the rod 14.

A slide piston 34 is located within the bore 26. The slide piston 34 has an enlarged rear end 34R which fits closely within the bore 26 and is located just forwardly of the pin 32. The enlarged rear end 34R of the slide piston 34 insures that the slide piston 34 slides back and forth within the bore 26 and does not become wedged in position as a result of misalignment. The front end 34F of the slide piston 34 is cut down and an O-ring 36 (of e.g. Teflon®) is located at the front end 34F of the slide piston 34. This seals the mechanism and prevents foreign matter (e.g. blood, body fluids etc.) from entering from the open front end 28 of the rod 14.

The operation of the preferred embodiment of the invention will now be explained with simultaneous reference to FIGS. 3 and 4. As has been described above, the invention is designed for use with a spring-loaded tool 2 which is threaded onto the threaded forward end 28 of the rod 14. This spring pressure always urges the slide piston 34 to the left as viewed in FIGS. 3 and 4. Consequently, when a tool 2 has been attached to the forward end 28 of the actuator 6', the slide piston 34 and the pin 32 are always pressed together and a movement of one part will cause all other parts to move as well.

One cycle of operation of the preferred embodiment will now be described. Let it be initially assumed that a tool 2 has been threaded onto the front end 28 of the actuator 6'. In this case, spring pressure will move the slide piston 34 to the left as viewed in FIGS. 3 and 4. This will push the pin 32 to the left and the trigger retainer 22 will be pushed to its extreme left position. The triggers 20 will then be fully rotated so that their free ends 20F are at their radially outermost positions and the elastomeric boot 12 which encloses the triggers 20 has its maximum diameter.

When a surgeon squeezes the elastomeric boot 12 between his thumb and index finger, or when a surgeon presses against the boot 12 with e.g. his index finger, force will be applied to at least one of the triggers 20. This will cause the trigger retainer 22 to move to the right and will cause all the triggers 20 to pivot together. This gives the surgeon the tactile sensation that his pressure against the spring loading from the tool 2 causes the boot 12 to collapse smoothly. As the trigger retainer 22 moves to the right, the pin 32 moves with it. The pin 32 in turn pushes the slide piston 34, which moves to the right and operates the tool 2 against the pressure exerted by its spring.

When the surgeon wishes to permit the tool 2 to return to its unoperated position, he relaxes his pressure on the elastomeric boot 12. Spring pressure from the tool 2 then moves the slide piston 34 to the left, pushing the pin 32 and the trigger retainer 22 to the left and rotating the triggers 20 so their free ends 20F move radially outwardly.

It will be immediately evident that the surgeon can easily and conveniently rotate the preferred embodiment of the invention between his thumb and index finger without changing the state of operation of the tool 2. It will likewise be immediately evident that the surgeon can operate the tool 2 by pressing at any point on the actuation surface 10.

In the preferred embodiment, the triggers 20 use elongated tie arms 20T because this produces substantial translational movement of the trigger retainer 22 and slide piston 34 with only slight rotation of the triggers 20. At present, the movement of the slide piston 34 is considered to be sufficient to operate any tool 2 which may be connected to the actuator 6'. However, if future tools 2 require more movement, an alternate embodiment exists which amplifies the translational movement of the piston 32 with respect to the translational movement of the trigger retainer 22. This alternate embodiment will now be described with reference to FIGS. 5 and 6.

In this alternate embodiment, the boot (not shown, but identical to the boot 12) surrounding the actuator 6' conceals from view two sets of mechanical components. The first set is very similar to the structure of the preferred embodiment of the invention; this set of components converts radial motion of the triggers 20 into linear translation motion within the actuator 6'. In the second set, this translation motion is amplified to provide motion which is adequate to operate any attached tool 2. The first set will be briefly described first, and the second set will be described next.

Figure 5:
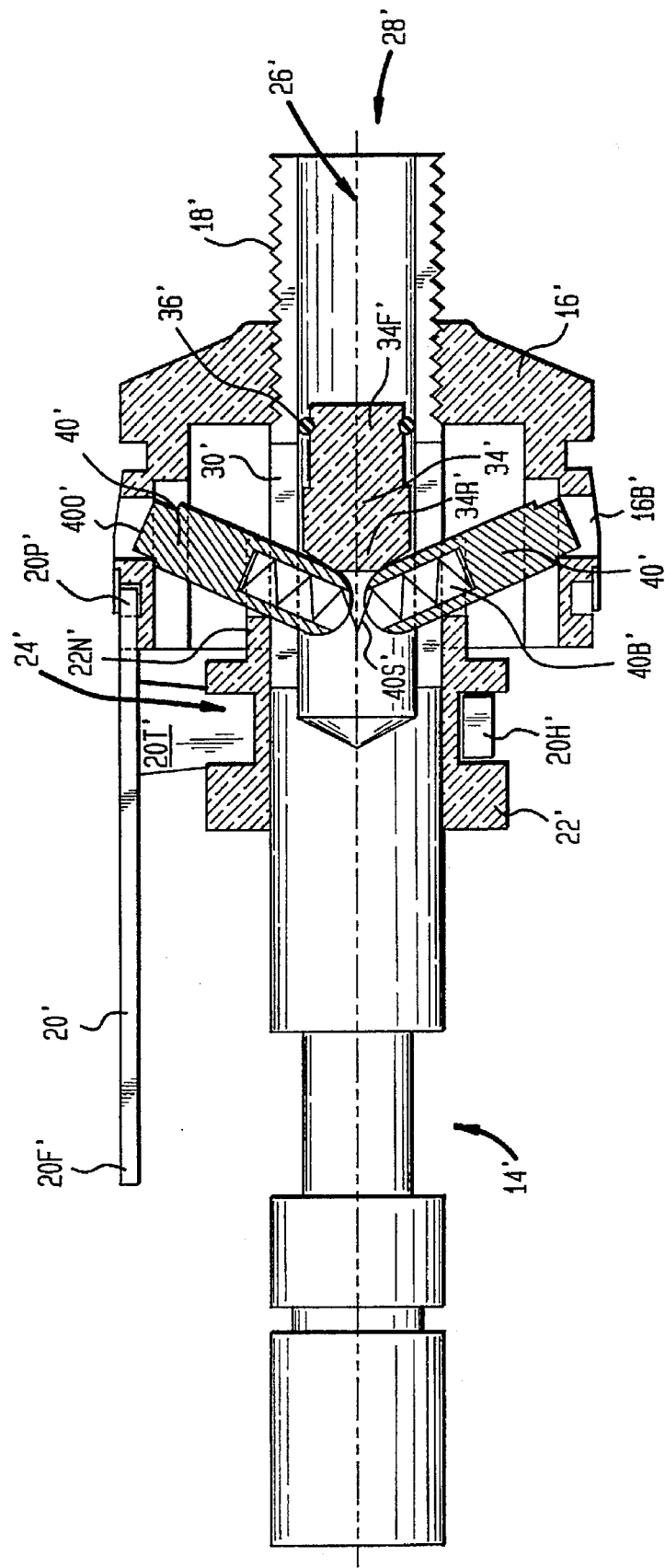
FIG. 5 shows a cross-sectional view of an alternate embodiment in the unactuated state, without the elastomeric boot.
Figure 6:
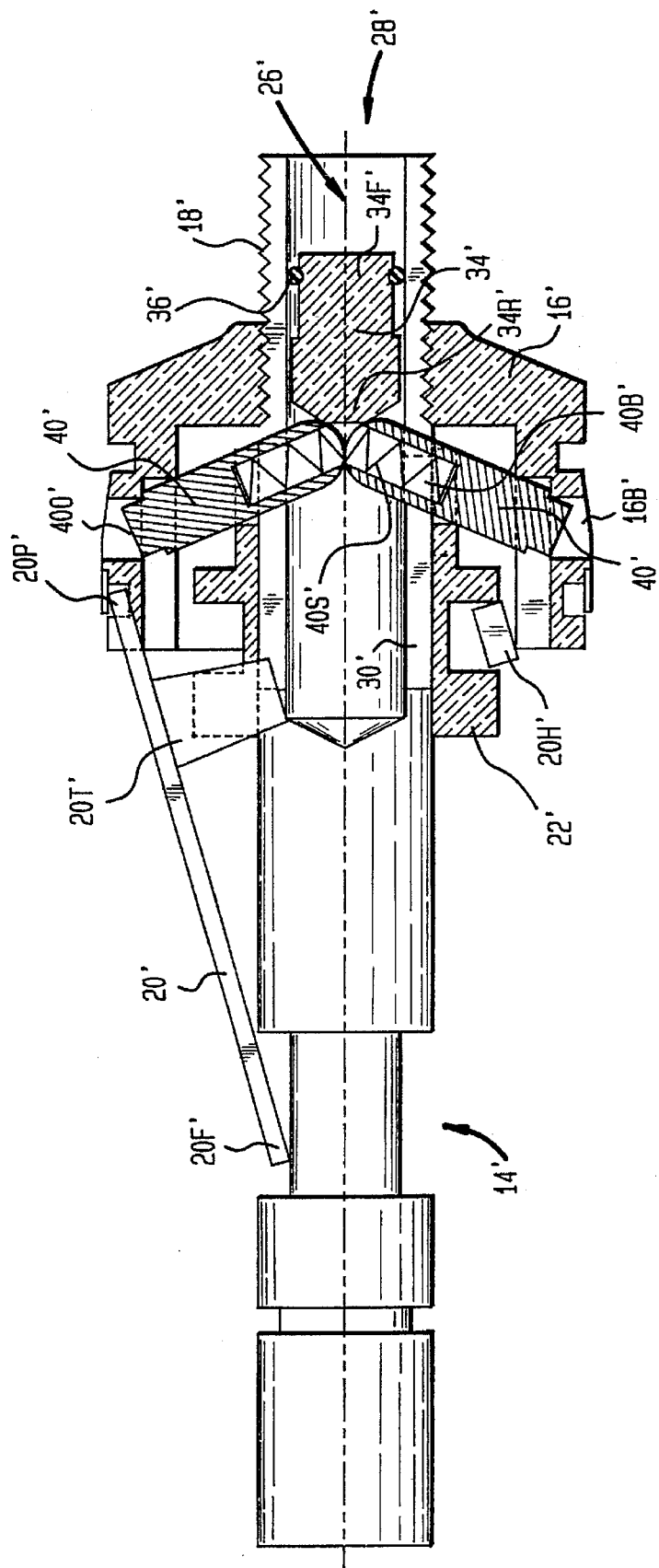
FIG. 6 shows a cross-sectional view of the FIG. 5 embodiment in the actuated state, without the elastomeric boot.

A central axially elongated rod 14' (the rod 14' is identical to the rod 14 in the preferred embodiment) supports a nose piece 16', which is fixed to the forward end 28' of the rod 14'. Six triggers 20' (for clarity, only one is shown in FIGS. 5 and 6) are pivotally secured to the nose piece 16'. The triggers 20' are the same as the triggers 20 in the preferred embodiment, and each trigger 20' has a pivot end 20P', a free end 20F' and a tie arm 20T'; each tie arm 20T' is curved to circulate around the rod 14', and each tie arm 20T' has a 20H' hook at its distal end. The boot (not shown, the same as the boot 12 in the preferred embodiment) fits over the nose piece 16' and triggers 20' and is sufficiently elastic to permit the triggers 20' to move radially inwardly and outwardly.

A trigger retainer 22' is slidably mounted upon the rod 14'. The trigger retainer 22' is similar to, but not the same as, the trigger retainer 22 in the preferred embodiment. Further as in the preferred embodiment, radial motion of the triggers 20' is converted to longitudinal motion of the trigger retainer 22'; this mechanical action is the same as described in connection with the preferred embodiment.

It is at the front end of the trigger retainer 22'where there are differences with respect to the trigger retainer 22 in the preferred embodiment. As stated above, the front end of the trigger retainer 22' cooperates with a second set of components which amplifies the motion of the trigger retainer 22' so that the slide piston 34' has a longer stroke than does the slide piston 34 in the preferred embodiment.

The front end of the trigger retainer 22' is formed into a notched sleeve 22N'. Immediately ahead of the notched sleeve 22N' are two pins 40'. The radially inner ends of the pins are located within the slot 30', and the rear surfaces of the central regions of the pins 40' are always engaged by the notches of the notched sleeve 22N'. A slide piston 34' is located within the bore 26' in the rod 14'; the slide piston 34' is identical to the slide piston 34 in the preferred embodiment.

The operation of this second set of components will now be explained with simultaneous reference to FIGS. 5 and 6. As has been described above, the invention is designed for use with a spring-loaded tool 2 which is threaded onto the threaded forward end 28' of the rod 14'. This spring pressure always urges the slide piston 34' to the left as viewed in FIGS. 5 and 6. Consequently, when a tool 2 has been attached to the forward end 28' of the actuator 6', the piston 34', the pins 40', the notched slide 22N' and the trigger retainer 22' are always pressed together and a movement of one part will cause all the other parts to move as well.

The radially outer ends 400' of the pins 40' are cut down to fit into bores 16B' in the nose piece 16'. This leaves the pins 40' free to pivot but insures that their radially outer ends 400' are retained at their radial stations with respect to the axis of the rod 14'. Furthermore, the pins 40' fit closely within the slot 30'. The pins 40' are therefore constrained to rotate within a plane about their radially outer endpoints 400'. As can be seen in FIGS. 5 and 6, each of the pins 40' operates as a lever having a fulcrum at its radially outer endpoint 400', a load adjacent its radially inner endpoint and a force applied by the notched sleeve 22N' intermediate its endpoints. The load moved by this type of lever will always move further than the distance over which the force is applied, i.e. this type of lever has a mechanical advantage which is greater than unity. Thus, the notched sleeve 22N', pins 40' and piston 34' amplify the translational motion of the trigger retainer 22'. In this alternate embodiment, a displacement of 0.060" (approximately 1.5 mm) of the trigger retainer 22' corresponds to a 0.100" (approximately 2.5 mm) displacement of the piston slide 34'. The exact mechanical advantage is determined by the ratio between a) the overall length of the pins 40' and b) the position on the pins 40' where the notched sleeve 22N' touches the pins 40'.

One cycle of operation of this alternate embodiment will now be described. As before, it is initially assumed that a tool 2 has been threaded onto the front end 28' of the actuator 6'. In this case, and as is shown in FIG. 5, spring pressure will move the slide piston 34' to the left, the pins 40' will be rotated to their fully unactuated positions, and the notched slide 22N' and the trigger retainer 22 will be at their extreme left positions. The triggers 20' will then be fully rotated so that their free ends 20F' are at their radially outermost positions and the elastomeric boot (not shown, but identical to the boot 12) which encloses the triggers 20' has its maximum diameter.

When a surgeon squeezes the elastomeric boot between his thumb and index finger, or when a surgeon presses against the boot with e.g. his index finger, force will be applied to at least one of the triggers 20'. This will cause the trigger retainer 22' to move to the right (FIG. 6) and will cause all the triggers 20' to pivot together. As in the preferred embodiment, this gives the surgeon the tactile sensation that his pressure against the spring loading from the tool 2 causes the boot to collapse smoothly. As the trigger retainer 22' moves to the right, it pushes the notched sleeve 22N' to the right, which applies force to the middle regions of the pins 40'. As discussed above, the translational motion of the trigger retainer 22 and the notched sleeve 22N' is amplified by the pins 40'. Thus, the radially inner ends of the pins 40' move to the right by a distance which exceeds the translational motion of the notched sleeve 22N', and this amplified motion is transmitted to the slide piston 34', which moves to the right and operates the tool 2 against the pressure exerted by its spring.

When the surgeon wishes to permit the tool 2 to return to its unoperated position, he relaxes his grip on the elastomeric boot. Spring pressure from the tool 2 then moves the slide piston 34' to the left, pushing the radially inner ends of the pins 40' to the left, moving the notched slide 22N' and trigger retainer 22' to the left and rotating the triggers 20' so their free ends 20F' move radially outwardly.

Now that the basic operation of the preferred embodiment and an alternate embodiment have been described, certain construction details will be discussed.

Both embodiments described herein utilize handles 4'. This is because such handles are conventional in this type of ophthalmic instrument. However, the use of a handle is not required. In the alternate embodiment, each of the pins 40' has an axially extending bore 40B' extending inwardly from its radially inner end. A compression spring 40S' of light-gauge wire is supported within the bores 40B' so as to bias the pins 40' in a radially outward direction. The purpose of this spring 40S' is to insure that the radially inner ends of the pins 40' always move together and to prevent the pins 40' from becoming misaligned within the device.

In both the preferred and alternate embodiments, the nose piece 16, 16' has the general shape of a cup with an open top and a hole in the center of the bottom. The nose piece 16, 16' is threaded onto the threaded end 28, 28' of the rod 14, 14' and is prevented from sliding rearwardly by an annular stop ridge (not shown) on the rod 14, 14'. In the alternate embodiment, the nose piece 16' has two small diametrically opposed bores 16B' which receive the projections of the pins 40'. This allows the pins 40' to pivot during operation while preventing the radially outer endpoints 400' of the pins 40' from moving radially outwardly. Outwardly extending tangs on the pivot ends 20P, 20P' of the triggers 20, 20' engage corresponding notches in the nose piece 16, 16' so that the triggers 20, 20' can pivot about their pivot ends 20P, 20P'; the triggers 20, 20' are positively retained in the nose piece 16, 16' by a snap ring (not shown). The elastomeric boot (e.g. 12) slides over the front of the nose piece 16, 16' and covers the circumferential surface of the nose piece 16, 16', the snap ring and the triggers 20, 20'; the rear end of the boot (e.g. 12) contains an eyelet (e.g. 12E, FIG. 3) and is retained in position on the rod 14, 14'. In this way, the entire mechanism is sealed and blood or other body fluids cannot enter into it from the outside to cause corrosion and necessitate cleaning.

While in accordance with the preferred embodiment the actuation surface 10 is generally cylindrical and coaxial with the handle, 4' this is not necessary. The surface 10 may be ribbed or polygonal and may be e.g. studded to provide a better grip.

While in accordance with the preferred embodiment the spring loading is provided by the attached tool 2, this is only because the preferred embodiment is designed to operate with tools 2 which are already on the market. It would alternatively be possible to provide the spring force using a spring within the handle 4' and to use non-spring-loaded tools.

In the described embodiments, six triggers 20, 20' are used, but this is not necessary. More or fewer triggers 20, 20' can be used instead. Six triggers 20, 20' are presently preferred because this produces a device which feels circumferentially continuous within the boot 12, but which can still be manufactured at reasonable cost.

In the alternate embodiment, a mechanism is used to amplify the actuation motion of the triggers 20'. This is not necessary; it is alternatively possible if required for the motion amplification mechanism to be replaced by a motion reduction mechanism.

Although a preferred embodiment has been described above, the scope of the invention is limited only by the following claims:

I claim:

1. A surgical instrument, comprising:
   an operable ophthalmic tool;
   an elongated handle having a longitudinal axis; and
   an actuator located at an end of the handle and connected in operative relation with the tool, the actuator causing operation of the tool by translational movement of an operator member and having a mechanism and an actuation surface mechanically coupled to the mechanism, the actuation surface extending completely around the longitudinal axis of the handle and the actuator and mechanism being operable by radially directed pressure exerted at any point on the actuation surface, said actuator including means for converting said radially directed pressure into axial translational motion of said operator member.

2. The instrument of claim 1, wherein the tool is detachably secured to the actuator.

3. The instrument of claim 1, wherein the actuator has a mechanical advantage which is greater than unity.

4. A surgical instrument for operating an ophthalmic tool which is detachably secured thereto, comprising:
   an elongated handle;
   an actuator located at an end of the handle, the actuator causing operation of the tool by translational movement of an operator member and having a mechanism and a generally cylindrical actuation surface which is generally coaxial with the handle and is mechanically coupled to the mechanism, the actuator and mechanism being operable by radially directed pressure exerted at any point on the actuation surface; and
   means for detachably securing the tool to the actuator in such a manner that when the tool is secured to the actuator, the tool is operated when the actuator and mechanism are operated by radially directed pressure exerted on the actuation surface, said actuator including means for converting said radially directed pressure into axial translational motion of said operator member.

5. The instrument of claim 4, wherein the actuation surface is a portion of an elastomeric boot.

6. The instrument of claim 4, wherein the actuator has a mechanical advantage which is greater than unity.

7. The instrument of claim 4, wherein the actuator comprises:
   means for amplifying said translational motion.

8. The instrument of claim 7, wherein said amplifying means comprises a lever.

9. The instrument of claim 8, wherein said amplifying means comprises two levers.

10. The instrument of claim 4, wherein the actuator comprises a plurality of elongated triggers which are regularly spaced around the handle.

11. A surgical instrument for operating an ophthalmic tool which is detachably secured thereto, the ophthalmic tool being of the type which is operated by moving a plunger against spring pressure, comprising:
    an elongated handle;
    an actuator located at an end of the handle and having a mechanism and a generally cylindrical actuation surface which is generally coaxial with the handle and is mechanically coupled to the mechanism, the actuator and mechanism being operable by radially directed pressure exerted at any point on the actuation surface and having a piston which moves axially when the actuator and mechanism are operated, said actuator including means for converting said radially directed pressure into axial translational motion of said piston; and
    means for detachably securing the tool to the actuator in such a manner that when the tool is secured to the actuator, the plunger and the piston abut each other.

12. The instrument of claim 11, wherein the actuator further comprises means for amplifying said translational motion, said amplifying means having a mechanical advantage which is greater than unity.

* * * * *